US006627665B2

(12) United States Patent
Waldron et al.

(10) Patent No.: US 6,627,665 B2
(45) Date of Patent: Sep. 30, 2003

(54) NON-DUSTING COPPER PYRITHIONE DISPERSION

(75) Inventors: Craig Waldron, Wolcott, CT (US); Patrick Hobbs, Dublin (IE)

(73) Assignee: Arch Chemicals, Inc., Norwalk, CT (US)

( * ) Notice: Subject to any disclaimer, the term of this patent is extended or adjusted under 35 U.S.C. 154(b) by 0 days.

(21) Appl. No.: 09/967,122

(22) Filed: Sep. 28, 2001

(65) Prior Publication Data

US 2003/0073749 A1 Apr. 17, 2003

(51) Int. Cl.$^7$ .................... A01N 25/04; A01N 55/02; A61K 9/10; C07F 1/08; C09D 5/16
(52) U.S. Cl. ................ 516/77; 106/18.33; 514/188; 514/937; 516/31; 523/122
(58) Field of Search ................ 514/188, 937; 516/31, 77; 106/18.33; 523/122

(56) References Cited

U.S. PATENT DOCUMENTS

| 4,323,683 A | | 4/1982 | Bolich, Jr. et al. ............... 546/6 |
|---|---|---|---|
| 4,345,080 A | * | 8/1982 | Bolich, Jr. ...................... 546/6 |
| 4,625,587 A | | 12/1986 | Hosono ........................ 74/752 |
| 4,898,621 A | | 2/1990 | Pruehs et al. ............... 134/25.2 |
| 5,057,153 A | * | 10/1991 | Ruggiero ................ 514/188 X |
| 5,137,569 A | * | 8/1992 | Waldron et al. ........ 514/188 X |
| 5,185,033 A | * | 2/1993 | Hani et al. .............. 514/188 X |
| 5,238,490 A | | 8/1993 | Farmer, Jr. et al. ...... 106/18.33 |
| 5,246,489 A | | 9/1993 | Farmer, Jr. et al. ...... 106/18.33 |
| 5,319,000 A | | 6/1994 | O'Connor et al. .......... 523/122 |
| 5,540,860 A | * | 7/1996 | Hosseini et al. ......... 514/188 X |
| 5,650,095 A | * | 7/1997 | Hosseini et al. ......... 514/188 X |
| 6,017,562 A | * | 1/2000 | Kaufman et al. ....... 514/188 X |
| 6,242,007 B1 | * | 6/2001 | Mohseni et al. ........ 514/188 X |
| 6,432,432 B1 | * | 8/2002 | Mohseni et al. ........ 514/188 X |

FOREIGN PATENT DOCUMENTS

WO  WO 00/54589  * 9/2000

OTHER PUBLICATIONS

"Particle Size–Selective Sampling Criteria for Airborne Particulate Matter" found in the "2002 Threshold Limit Values and Biological Exposure Indices" published by the American Conference of Governmental Industrial Hygienists.

* cited by examiner

Primary Examiner—Richard D. Lovering
(74) Attorney, Agent, or Firm—Dale Lynn Carlson; Wiggin & Dana LLP

(57) ABSTRACT

The present invention is directed to a non-dusting copper pyrithione dispersion, comprising an admixture of: from about 20 to about 99 wt % of copper pyrithione; from about 0.05 to about 30 wt % of a dust-inhibiting agent selected from the group consisting of surfactants, polymer resins, binders, and combinations thereof; and from about 0.05 wt. % to about 80 wt % of a dispersant; wherein all weight percents are based on the total weight of the dispersion.

23 Claims, No Drawings

NON-DUSTING COPPER PYRITHIONE DISPERSION

BACKGROUND OF THE INVENTION

1. Field of the Invention

The present invention relates generally to copper pyrithione compositions, and more particularly to a non-dusting copper pyrithione dispersion of solid copper pyrithione particles dispersed in water or an organic dispersant. The dispersion additionally contains a dust-inhibiting agent selected from the group consisting of surfactants, polymer resins, binders, and combinations thereof.

2. Description of the Related Art

Pyrithione salts are well known compounds useful in a wide variety of applications including biocides such as fungicides and bactericides. Heavy metal salts of pyrithione, including zinc, tin, cadmium and zirconium, as well as the magnesium and aluminum salts, in the form of flat platelets suitable for use in shampoo, are disclosed in U.S. Pat. Nos. 4,345,080 and 4,323,683. For example, paints containing a pyrithione salt (e.g. zinc or sodium pyrithione) plus a copper salt (e.g. cuprous oxide or cuprous thiocyanate) are known in the art, as disclosed, for example, in U.S. Pat. No. 5,057,153.

U.S. Pat. No. 5,185,033 describes a process for making a paint or paint base containing copper pyrithione or pyrithione disulfide plus cuprous oxide, wherein the paint exhibits stability against gelation during storage.

U.S. Pat. No. 5,246,489 discloses a process for providing in situ generation of copper pyrithione in a paint or paint base which comprises incorporating a metal salt of pyrithione, cuprous oxide and a controlled amount of water into the paint either during or after the formation of the paint.

In many applications, copper pyrithione offers several advantages over other forms of pyrithione such as zinc pyrithione. For example, copper pyrithione is more stable than zinc pyrithione when added to paint products and therefore is less likely to cause gelation during storage.

Commercially available copper pyrithione is typically sold as a dry powder, which easily generates dust. Copper pyrithione powder was shown to be more toxic than zinc pyrithione powder when tested for acute inhalation toxicity in rats. The copper pyrithione dust can pose an inhalation hazard when handling powder in poorly ventilated areas. The advantage of a non-dusting copper pyrithione product over the powder product is the significant reduction of the inhalation hazard to the customers and/or the employees working with the non-dusting product, as compared to the powder.

Certain non-dusting forms of copper pyrithione have been previously disclosed. More specifically, PCT publication WO00/54589 discloses coated copper pyrithione particles having a coating selected from among glycerol, dialkyl phthalates, lubricating oils, acrylic resins, rosins, fatty acid amides, dialkylpolysulfides, polybutene, paraffins, and vaseline. Unfortunately, the process of producing these coated particles typically necessitates the cumbersome steps of mixing/kneading or distillation of solvent under reduced pressure, as described on the page preceding the working examples of the WO00/54589 publication. Accordingly, what is now needed is simpler methodology for providing non-dusting copper pyrithione. The liquid/solid dispersions of the present invention provide one answer to that need.

SUMMARY OF THE INVENTION

In one aspect, the present invention is directed to a non-dusting copper pyrithione dispersion of solid copper pyrithione in a liquid dispersant. More specifically, the dispersion comprises (a) from about 20% to about 99% (preferably from about 20% to about 70%) by weight of solid copper pyrithione particles dispersed in (b) from about 0.05% to about 80% by weight of a liquid dispersant selected from the group consisting of water, organic solvents, and combinations thereof. The dispersion additionally comprises (c) from about 0.05% to about 30% of a dust-inhibiting agent selected from the group consisting of surfactants, polymer resins, binders, and combinations thereof. All of these weight percents are based on the total weight of the dispersion.

In another aspect, the present invention is directed to a method of making a non-dusting copper pyrithione dispersion by dispersing component (a) in component (b), either prior to, simultaneously, or after, combining dust inhibiting additive (c) with component (b) in order to prepare the desired dispersion comprising (a) plus (b) plus (c).

A dispersion of solid non-dusting copper pyrithione particles in a liquid dispersant, said copper pyrithione particles being coated with a coating compound selected from the group consisting of hydrocarbon resin monomer produced from co-polymerization of vinyltoluene and alpha-methylstyrene, rosins, polystyrene, cellulose, shellac, acrylic polymers, poly-D,L-lactic acid, poly-D,L-lactic-co-glycolic acid, zein, polymer esters of dicarboxylic acids, polyvinylacetate phthalate, polyvinyl alcohol, polyacrylic acid, ethyleneglycol, polyvinyl pyrrolidone, sodium lignosulfonate, chitosan, guar gums, polysaccharides, and combinations thereof.

These, and other aspects of the present invention, will become apparent upon reading the following detailed description of the invention.

DETAILED DESCRIPTION OF THE INVENTION

The present invention provides an improved solution to the dusting problem typically associated with dry powders of copper pyrithione. The present inventors have solved this problem combining copper pyrithione with one or more dust-inhibiting agents in a solvent to provide a substantially non-dusting or dust-free copper pyrithione composition. The non-dusting or dust-free copper pyrithione composition of the present invention takes the form of a solid/liquid dispersion. This solid/liquid dispersion is easy to handle, minimizing solids handling problems, and reducing or eliminating the risk of inhalation exposure of airborne levels of copper pyrithione. Moreover, the inclusion of a dust-inhibiting component in the dispersion of the present invention contributes both to the inhibition of dust formation from the dispersion, and to the inhibition of the formation of gels or thick thixotropic precipitates, thus contributing to an enhanced shelf life for these dispersions.

As used herein, the term "dispersion" is intended to encompass both low viscosity solid/liquid admixtures, and higher viscosity solid/liquid compositions, such as pastes. Generally, the viscosity of the dispersion is in the range of from about 1,000 cps to about 100,000 cps at room temperature, preferably between about 5,000 cps and 70,000 cps at room temperature, wherein "cps" denotes Centipoise.

As used herein, the terms "non-dusting" and "dust-free" refer to a composition that is substantially free, advantageously greater than least 99% by weight free, of airborne copper pyrithione particles. The term "dust-inhibiting agent" refers to compounds that prevent or inhibit the formation of dust, as compared to a composition that does not include those compounds. "Airborne particles" are described in detail under the "Sampling Criteria for Airborne Particulate Matter" found in the "1999 Threshold Limit Values and Biological Exposure Indices" published by the American Conference of Governmental Industrial Hygienists. More specifically, that publication states that, for chemical substances present in inhaled air as suspensions of solid particles or droplets, the potential hazard associated with airborne particles depends on particle size as well as mass concentration.

As indicated above, the present invention is a non-dusting copper pyrithione dispersion comprising copper pyrithione, a dispersant, and a dust-inhibiting compound selected from the group consisting of surfactants, polymer resins, binders, and combinations thereof. Each of these components is discussed in more detail below.

Copper pyrithione is available commercially (from Arch Chemicals, Inc., Norwalk, Conn.) in the form of a dry powder. This form of copper pyrithione may be used directly in the dispersion of the invention, or copper pyrithione may be made my conventional methods known in the art, as disclosed in U.S. Pat. Nos. 5,650,095; 5,540,860; 5,238,490, all of which are incorporated by reference herein. Briefly, copper pyrithione may be made by reacting a copper salt and/or copper oxide and a pyrithione salt in an aqueous or organic carrier medium. Suitable pyrithione salts are those which are soluble in the organic or aqueous carrier, such as sodium, calcium, potassium, and magnesium salts of pyrithione, pyrithione acid or the non-metal salts such as the ethanolamine salt, chitosan salt, and the disulfide salt of pyrithione (which is commercially available from Arch Chemicals, Inc. as "OMADINE MDS"). The pyrithione salt is preferably employed in an amount of between about one and about 40 weight percent, more preferably between 5 and 25, and most preferably between about 15 and 25 weight percent, all weight percents being based on the total weight of the reaction mixture, in order to prepare the desired copper pyrithione.

The copper salt is suitably any salt containing copper that is soluble in the carrier employed in the reaction. For example, if water is the carrier, useful copper salts include copper chloride dihydrate, copper sulfate, copper carbonate, copper nitrate, copper acetate, as well as combinations thereof. The above copper salts may be used individually or in combination, or in combination with copper oxide.

The copper salt, or copper salt/copper oxide combination, used to prepare copper pyrithione is preferably employed in an amount of between about one and about 50 weight percent, more preferably between 5 and 30 weight percent, and most preferably between about 15 and 20 weight percent, all weight percents being based on the total weight of the reaction mixture.

Carriers that are useful in the reaction mixture for preparing the copper pyrithione include water, organic solvents, and combinations thereof. Useful organic solvents include alcohols such as methanol and ethanol, amines such as diethanolamine, ethers, esters, and the like.

The non-dusting copper pyrithione composition is produced by dispersing the copper pyrithione prepared as described above in an aqueous or organic dispersant, and incorporating a dust-inhibiting agent prior to, simultaneously with, or after, performing the dispersing step. Illustrative organic dispersants include xylene(s), alcohols such as methanol, ethanol, ethers, esters, and combinations thereof. The amount of dispersant used in the present invention will be the balance of the dispersion as compared to the other components, and generally represents from about 1 to about 80 wt %, preferably from 10 wt % to 80 wt %, based upon the total weight of the dispersion.

The copper pyrithione is preferably employed in the dispersion in an amount of between about 20 and 99 wt %, more preferably between about 30 and 70 wt %, even more preferably between about 30 and 50 wt %, and most preferably between about 40 and about 55 wt %. All weight percents are based upon the total weight of the dispersion. A particularly useful amount of copper pyrithione is about 45 wt %.

The dust-inhibiting component of the composition of the present invention is preferably one or more surfactants, one or more polymer resins, one or more binders, or combinations thereof. Generally, this component comprises from about 0.05 to about 30 wt % of the composition of the invention. Particularly useful dust-inhibiting additives that are useful for inclusion in the dispersion are the copolymer of vinyltoluene and alpha-methylstyrene, rosins, polystyrene, cellulose, shellac, acrylic polymers, poly-D,L-lactic acid, poly-D,L-lactic-co-glycolic acid, zein, polymer esters of dicarboxylic acids, polyvinylacetate phthalate, polyvinyl alcohol, polyacrylic acid, ethyleneglycol, polyvinyl pyrrolidone, sodium lignosulfonate, chitosan, guar gums, polysaccharides, and combinations thereof.

Suitable surfactants employed in the composition of the present invention may be selected from the classes of surfactants known as nonionics, anionics, cationics, and amphoterics (the latter being also commonly referred to as "zwitterionics"). The surfactants are suitably employed singly, or in combinations of two, three, or even four surfactants selected from the above-mentioned four classes of surfactants. When used singly, nonionics are preferred, although the anionic surfactants were also found to provide good results. Although less preferred when employed as the sole surfactant, the cationics and amphoteric surfactants provided an improvement in reducing the extent of the gelation problem during production of the copper pyrithione dispersion prepared without employing any surfactant.

Useful nonionic surfactants include linear alcohol alkoxylates, such as the linear alcohol ethoxylates, ethoxylated/propoxylated block copolymers, ethoxylated/propoxylated fatty alcohols, and polyoxyethylene cetyl ethers, and the like. Useful linear alcohol alkoxylates are commercially available, for example, under the registered trademark POLY-TERGENT SL-42, a product of Arch Corporation. If desired, the alcohol alkoxylate is suitably end-capped with a lower alkyl group, and such a product is commercially available as POLY-TERGENT SLF-18, a propylene oxide-capped linear alcohol alkoxylate that is also a product of Arch Chemicals Corporation, and these end-capped linear alcohol alkoxylates are notably low foaming during use. Also advantageous for use in accordance with the present invention are surfactants within the group commercially available as POLY-TERGENT SLEF-18B series surfactants, which are surfactants characterized by enhanced biodegradability (also products of Arch Chemicals Corporation), being alkene oxide-capped linear alcohol alkoxylates, containing ethylene oxide moieties in the backbone, and suitably also containing at least one propylene oxide moiety in the backbone, as disclosed for example, in U.S. Pat. Nos. 4,925,587 and 4,898,621.

Other useful nonionic surfactants include one commercially available as NEODOL 91-6, a trademarked surfactant product of Shell Chemical. This surfactant is a detergent range mixture of C9–C11 linear primary alcohol ethoxylates having an average of six moles of ethylene oxide per mole of alcohol. Other useful nonionic surfactants include those containing a linear C9–C11 carbon chain and five or six ethylene oxide or propylene oxide groups per molecule.

Useful anionic surfactants include alkyl diphenylether disulfonates, alkyl phenyl ethoxylated phosphate esters, carboxylated linear alcohol alkoxylates, linear alkyl benzene sulfonic acid, diisobutyl sulfosuccinate, abietic acid and alkyl sulfonates.

Other useful anionics are polycarboxylated alcohol alkoxylates, preferably those selected from the group consisting of the acids or organic or inorganic salts of the following: polycarboxylated linear alcohol alkoxylates, polycarboxylated branched alcohol alkoxylates, polycarboxylated cyclic alcohol alkoxylates, and combinations thereof. These polycarboxylated alcohol alkoxylates typically contain at least two succinic acid radicals per molecule. Preferred polycarboxylated alcohol alkoxylates are those having a backbone containing both poly(propylene oxide) and poly(ethylene oxide) blocks, and such preferred polycarboxylated alcohol alkoxylates are readily commercially available, for example, as POLY-TERGENT CS-1, a trademarked surfactant of Arch Chemical Corporation. The polycarboxylated alcohol may also contain a polycarboxylic acid, for example, polyacrylic acid, along with the starting alcohol alkoxylate and esters of the alkoxylate of the polycarboxylic acid.

Although individually the cationic and the amphoteric surfactants are acceptable for use in the process of the present invention, it is preferred that they be used in combination with at least one surfactant from one of the other classes. Illustrative cationics include alkyl triammonium halide, non-linear alkyl dimethyl halide and alkyl dimethyl benzyl ammonium halide containing surfactants. Illustrative amphoteric surfactants include polyglycol ether derivatives, ethoxylate oxazolin derivatives, lauramidopropyl betain and lecithin.

Suitable blends can be employed in the process of the present invention based on various combinations of the above-described surfactants. Such a blend can be any combination of two or more surfactants, between or within the above-described four broad classes of surfactants. Combinations can include blends of: anionic with anionic, anionic with nonionic, anionic with cationic, anionic with amphoteric, cationic with cationic, cationic with amphoteric, nonionic with nonionic, nonionic with amphoteric, and amphoteric with amphoteric. Likewise, ternary and quaternary blends of surfactants by selecting three or four surfactants, respectively, from within or among the above-described classes.

Suitably, any single or combination of two, three or four surfactants from the following illustrative list are suitably employed: (a) nonionics, including alkoxylated linear alcohols (such a POLY-TERGENT SLF-18 surfactant, a product of Arch Chemicals Corporation), linear alcohol ethoxylates (such as NEODOL 91-8 surfactant, a product of the Shell Corporation), ethoxylated liner alkyl benzene (such as TRITON X-100 surfactant, a produce of Union Carbide Corporation), and EO/PO block copolymers (such as POLY-TERGENT E-17A surfactant, a product of Arch Chemicals Corporation); (b) anionics, including alkyl diphenyl ether disulfonates (such as POLY-TERGENT 2A1 surfactant, a product of Arch Chemicals Corporation), alkyl phenyl ethoxylated phosphate esters (such as Wayfos M-60 surfactant, a product of Arch Chemicals Corporation), carboxylated linear alcohol alkoxylates (such as POLY-TERGENT CS-1 surfactant, a product of Arch Chemicals Corporation). linear alkyl benzene sulfonic acid (such as BIOSOFT S-130 surfactant, a product of Stepan Company), alpha-olefin sulfonates (such as BIO TERG AS-40 surfactant, a product of Stepan Company), dialkylsulfosuccinates (such as AROWET SC-75 surfactant, a product of Arol Chemical Products), and alkyl sulfates (such as STEPANOL SLS surfactant, a product of Stepan Company); (c) cationics including alkyl triammonium halides (such as CTAB surfactant, a product of VWR Scientific, Inc.), polyoxyethylene cocoamine (such as MAZERN surfactant, a product of PPG Industries), primary alkyl amines (such as ARMEEN surfactant, a product of Akzo Chemical Co.), dicoco dimethyl ammonium halide (such as JET QUAT surfactant, a product of Jetco Chemical Inc.), di-isodecyl dimethyl ammonium halides (such as AMMONYX K9 surfactant, a product of Stepan Company), and diethyl aminoethyl stearate (such as CERASYNT 303 surfactant, a product of ISP Van Dyke); and, (d) amphoterics, including polyglycol ether derivatives (such as ALBEGAL A surfactant, a product of Ciba-Geigy), ethoxylated oxazolin derivatives (such as ALKATERG T-IV surfactant, a product of Angus Chemicals), lauramide propyl betaine (such as LEXAINE C surfactant, a product of Inolex Chemicals), lecithin (such a CANAPERSE surfactant, a product of Can Amoral), disodium cocoamphodiacetate (such as MONATERICS surfactant, a product of Mona Industries), complex fatty amine salt (such as MAFO 13 surfactant, a product of PPG Industries), and cocoamine oxide (such as MACKAMINE CO surfactant, a product of the McIntyre Group Ltd.).

The surfactant or surfactants are preferably employed in a total amount of between about 0.05 and about 10% by weight, more preferably between 0.1 and about 5% by weight, and most preferably between about 0.5 and about 2% by weight, all weight percents being based upon the total weight of the dispersion.

Suitable resins for use as the dust-inhibiting component in the composition of the present invention include acrylic resins, vinyl resins, alkyd resins, epoxy resins, polyurethane resins, natural resins, rosins, polyester resins, plastisols, and combinations thereof. Vinyl resin is particularly useful in the composition of the present invention.

Plastisols useful in the dispersion of the present invention comprise a resin plus a carrier, such as a plasticizer, as described in U.S. Pat. No. 5,319,000, herein incorporated by reference in its entirety, including commercially available plastisols containing plasticizers and resin-compatible additives. Useful plastisols with the carriers, for example, include adipic acid derivatives such as diisobutyl adipate, di-n-hexyl adipate, heptyl nonyl adipate, bis(2-ethylhexyl) adipate, diisodecyl adipate and bis(2-butoxyethyl)adipate; azelaic acid derivatives such as bis(2-ethylhexyl) azelate; benzoic acid derivatives such as diethylene glycol dibenzoate, dipropyleneglycol dibenzoate, and 2,2,4-trimethyl-1,3-pentanediol-isobutyrate benzoate; citric acid derivatives such as tri-n-butyl citrate and tri-n-butyl acetyl-citrate; epoxy derivatives such as epoxidized soybean oil, epoxidized linseed oil, 2-ethylhexyl epoxy tallate and bisphenol A diglycidyl ether; glycol derivatives such as diethylene glycol dipelargonate, triethylene glycol di-2-ethylbutyrate, and poly(ethylene glycol) (200) di-2-ethylhexanoate; glycolates such as methyl phthalyl ethyl glycolate and butylphthalyl ethyl glycolate; hydrocarbons such as hydrogenated terphenyls HB-40, poly(alkyl naphthalenes), PANAFLEX, aliphatic aromatics ("LEROMOLL") and chlorinated paraffin (52% wt % Cl) ("CERECLOR S-52"); isophthalic acid derivatives such as di-2-ethylhexyl isophthalate; oleic acid derivatives such as butyl oleate; phosphoric acid derivatives such as tributyl phosphate, tri-2-ethylhexyl phosphate, tributoxyethyl phosphate, chlorinated diphosphate ("PHOSGARD 2XC-20"), cresyl diphenyl phosphate, tricresyl phosphate, isopropylphenyl diphenyl phosphate ("KROTINEX 100"), t-butylphenyl diphenyl phosphate ("SANTICIZER 154"), 2-ethylhexyl diphenyl phosphate and isodecyl phosphate; phosphoric acid derivatives such as chlorinated polyphosphonate ("PHOSGARD C-22-R"); phthalic acid derivatives such as dimethyl phthalate, dibutyl phthalate, butyl octyl phthalate, diisohexyl phthalate, heptyl nonyl phthalate, heptyl nonyl undecyl phthalate, diisooctyl phthalate, dialkyl ($C_7$–$C_{11}$), ($C_6$–$C_{10}$) and ($C_8$–$C_{10}$) mixed linear phthalates ("SANTICIZER 711" or "PLATINOL 711P"), bis(2-ethylhexyl) phthalate, diisodecyl phthalate, diundecyl phthalate, ditridecylphthalate, butyl cyclohexyl phthalate, butyl benzyl phthalate, 7-(2,6,6,8-tetramethyl-4-oxa-3-oxononyl) benzyl phthalate, bis(2-butoxyethyl) phthalate, di(n-octyl) phthalate and dicyclohexyl phthalate; polyesters such as adipic acid polyester (mol wt 6000) ("PARAPLEX G-40"), adipic acid polyester (mol wt 2000) ("SANTICIZER 334F"), azelaic acid polyester (mol wt 850) ("PLASTOLEIN 9720"), azelaic acid polyester (mol wt 2200) ("PLASTOLEIN 9750") and sebacic acid polyester; ricinoleic acid derivatives such as methyl ricinoleate, n-butyl acetylricinoleate and castor oil (90 weight percent glyceryl ricinoleate); sebacic acid derivatives such as bis(2-ethylhexyl) sebacate; stearic acid derivatives such as butyl acetoxystearate; sucrose derivatives such as sucrose acetate-isobutyrate; sulfonic acid derivatives such as N-thyl-(o,p)-toluenesulfonamide and alkylsulfonic acid ester of phenol and cresol ("MESAMOLL"); terephthalic acid derivatives such as bis(2-ethylhexyl) terephthalate; and trimellitic acid derivatives such as tris(2-ethylhexyl) trimellitate, heptyl nonyl trimellitate, heptyl nonyl undecyl trimellitate and triisodecyl trimellitate.

Other useful carriers for the plastisol include additives not normally classified as plasticizers, such as polyols. An important criterion for the additive(s) useful as carriers within the scope of the present invention is that the additive (s) interacts with the selected swellable polymer resin upon heating to cause swelling of the polymer particles. In order for the carrier to be useful in a specific application, swelling of the polymer particles must occur at an elevated temperature below the degradation temperature of the polymer and of the carrier. Heat stabilizers can optionally be employed in order to provide elevated degradation temperatures.

The amount of carrier employed in the plastisol suitably ranges between about 20 and about 95, preferably between about 50 and about 85, weight percent based upon the total weight of the dispersion.

Suitable resins in plastisol useful in the present invention include, for example, the following resins and combinations thereof: cellulosics such as cellulose acetate, cellulose acetate-butyrate, cellulose nitrate, and ethylcellulose; polyacrylates such as poly(methyl methacrylate) and acrylic copolymers, polystyrenes; polyolefins such as polyethylene and polypropylene; polycarbonates; rubbers and synthetic elastomers; vinyl polymers such as poly(vinyl acetate), poly(vinyl butyral), poly(vinyl alcohol) and poly (vinylchloride); and polyacrylonitrile and modified copolymers thereof; and combinations thereof. The preferred resin is plastisol-grade poly(vinylchloride) ("PVC") which is typically made by emulsion polymerization and is commercially available, for example, as "GEON 125A", a product of the BF Goodrich Company.

Preferable amounts of the resin component of the plastisol generally range from between about 0.2% by weight and about 30% by weight, all weight percents being based upon the total weight of the plasticsol.

Useful binders that may be used in the composition of the present invention any low-melt polymer or wax known in the binding arts. Exemplary binders include rosins such as rosins sold under the trade name "TACOLYN" or "PICO-TEX" (hydrocarbon resin monomer produced from co-polymerization of vinyltoluene and alpha-methystyrene), acrylates such as methyl acrylate, ethyl acrylate, and the like, xanthate or guar gums, polyvinyl alcohol, ethyl acetate, and combinations thereof. Useful amounts of the binder component preferably range from about 0.1 to about 20 wt %, more preferably from about 0.5 to about 10 wt %, and most preferably from about 0.5 to about 5 wt %, all weight percents being based on the total weight of the composition.

As indicated above, the dust-inhibiting agent component of the composition of the present invention may be used individually (e.g., only a surfactant, or only a polymer resin as the dust-inhibiting component). Alternatively, combinations of one or more of the above-described dust inhibiting agents may be used as the dust-inhibiting component. Moreover, it is possible to employ one or more of the above-described dust-inhibiting agents (e.g., surfactants) in combination with one or more other dust-inhibiting agents (e.g., polymer resins) to produce the dust-inhibiting component of the present invention.

As indicated above, the copper pyrithione in the dispersion of the present invention may take the form of a fine, non-dusting powder, (e.g., a dispersion), or, alternatively, larger non-inhalable granules (e.g., greater than about 4 microns). Generally, the particle size range for the copper pyrithione in the dispersion is between about 0.01 micron and about 1,000 microns, preferably between about 0.01 micron and about 50 microns. Advantageously, at least about 90% of the particles in the dispersion have a particle size of less than 50 microns.

In a particularly advantageous dispersion of the present invention, the dust-inhibiting agent is preferably one or more surfactants and/or one or more polymer resins and/or one or more binders, and the non-dusting copper pyrithione dispersion is prepared generally as follows:

The selected polymer resin and/or surfactant is first added to a mixing vessel and dissolved in the solvent of choice with low speed mixing (generally from about 500–800 rpm) using a high speed disperser or another type of mixer or mill known in the paint and coating art. The copper pyrithione is next added, and the mixing speed is increased to between 5,000 and 10,000 rpm. Mixing is continued until a homogenous dispersion or paste is produced, generally from about 1 minute to about 4 hours, more preferably from about 5 minutes to about 90 minutes, and most preferably from about 5 minutes to about 45 minutes. The pH of aqueous dispersions are generally maintained in the range of pH 5–9.

If copper pyrithione wet filter cake is used to make an organic solvent based dispersion, remaining water must be removed from the final composition. In one embodiment, the above mixing step is done in a closed flask or reactor with a Dean-Stark trap connection or another device used for removing the water from the organic solvent. The mixture may be heated to between about 95° C. to 105° C. or higher until no more water is being removed from the dispersion.

Alternatively, the mixing can be done under vacuum with lower (or no) required heating temperatures.

The non-dusting copper pyrithione composition of the present invention may be made as a dispersion which takes the form of a thick paste. When made with water as the dispersant, the composition of the invention has a viscosity generally in the range of from about 1000 centipoise (cps) to about 7,500 cps at room temperature. The non-dusting copper pyrithione composition of the present invention made with an organic solvent has a viscosity generally in the range of from about 5,000 cps to about 100,000 cps (preferably 5,000 to about 70,000 cps) at room temperature.

The non-dusting copper pyrithione composition of the present invention offers significant advantages over the copper pyrithione compositions of the prior art. The non-dusting copper pyrithione dispersions of the present invention provide easy processing and mixing with paints, coatings, or personal care compositions, such as soaps, shampoos, medicaments, and the like. The dust-inhibiting properties of the present invention significantly reduces the presence of airborne copper pyrithione dust in the local environment. As a result, the non-dusting copper pyrithione dispersion of the present invention can be handled easily with reduced risk without fear of inhalation of toxic airborne copper pyrithione powder. In addition, it has been found that when the copper pyrithione dispersion is spilled and the solvent evaporates, the dust-inhibiting component in the dispersion forms a film on the copper pyrithione which minimizes dusting. Further, the dust-inhibiting component inhibits the formation of gels or thick thixotropic precipitates, and therefore increases the shelf life of the present composition.

EXAMPLES

The invention is further described by the following Examples, but is not intended to be limited by these Examples. All parts and percentages are by weight and all temperatures are in degrees Celsius unless explicitly stated otherwise. All weight percents are based on the total weight of each composition, unless explicitly stated otherwise.

Example 1—Preparation of a Copper Pyrithione (CuPT) Dispersion in an Organic Solvent 13 grams "LAROFLEX MP25" polymer resin (vinyl chloride-isobutyl vinyl ether copolymer, BASF Corporation, Charlotte, N.C.) was dissolved into 832 grams of xylene. Following dissolution of the polymer, 862 grams of copper pyrithione (Arch Chemicals ACBV Swords, Ireland) (49% by weight) was added slowly and with constant mixing using a high speed disperser at a speed of 1000–3500 RPMs. The mixture was stirred at low speed (1000 RPM) and with low shear to provide adequate mixing until a homogenous mixture was achieved. A rotor/stator type disperser (i.e. a Silverson type) or grinding mills (i.e. a bead or sand mill) can be used in place of a high speed disperser to achieve similar results.

The dispersion (1707 grams total) had the following composition:

| Component | Amount (g) | Wt % |
| --- | --- | --- |
| LAROFLEX MP25 (polymer) | 13 | 0.76 |
| Copper | 862 | 50 |

-continued

| Component | Amount (g) | Wt % |
| --- | --- | --- |
| pyrithione | | |
| Xylene solvent | 832 | 49 |

Example 2—Comparison Example

A procedure identical to Example 1 was conducted in absence of the polymer resin. Briefly, 832 grams of xylene was added to a beaker, and copper pyrithione powder (862 grams) was added slowly with continuous mixing using a using a high speed disperser at a speed of 1000–3500 RPMs. All of the copper pyrithione could not be charged into the beaker because the paste-like mixture began to thicken (only about 25% based on total weight of CuPT could be added). Additional stirring did not provide adequate mixing and no homogenous mixture was achievable. The resulting material was a very thick, unflowable paste of copper pyrithione.

Example 3—Preparation of a Copper Pyrithione (CuPT) Dispersion in Water 3 grams of "DARVAN" dispersing agent (sodium salt of copoly(naphthalene sulfonic acid/formaldehyde from R. T. Vanderbilt Company, Inc.) was dispersed into 75 grams of water. Following dissolution of the Darvan, 77 grams of copper pyrithione powder was added slowly with continuous mixing using a high-speed disperser (1000–3500 RPMs). Stirring was continued at low speed (1000 RPMs) with low shear to provide adequate mixing until a homogenous mixture is achieved. A rotor/stator type disperser (i.e. a Silverson type) or grinding mills (i.e. a bead or sand mill) can be used in place of a high speed disperser to achieve similar results.

The dispersion (155 grams total) had the following composition:

| Component | Amount (g) | Wt % |
| --- | --- | --- |
| DARVAN (surfactant) | 3 | 2 |
| Copper pyrithione | 77 | 50 |
| water | 75 | 48 |

Example 4—Preparation of a Copper Pyrithione (CuPT) Dispersion in an Organic Solvent from Wet Copper Pyrithione Filter Cake 13 grams "LAROFLEX MP25" polymer resin (vinyl chloride-isobutyl vinyl ether copolymer, BASF Corporation, Charlotte, N.C.) was dissolved into 832 grams of xylene in a 3 Neck 3-Liter flask with a Dean-Stark trap connected to one of the necks. Following dissolution of the polymer, 1188.6 grams of copper pyrithione wet filter cake containing ~30% water (Arch Chemicals ACBV Swords, Ireland) was added to the 3-neck flask. Mixing at a speed of 1000–3500 RPMs and heating with a heating mantle under the flask was started. The mixture was stirred at low speed (1000 RPM) and with low shear to provide adequate mixing until a homogenous mixture was achieved. The mixing speed was then increased to ~2500 RPM. A Ross Planetary mixer with dispersing blades can be used in place of this 3-neck flask set-up to achieve similar results. The mixture was heated to 95° C. to about 105° C. until the Dean-Stark trap was removing no more water. This took about 3 hours to complete.

The resulting dispersion (~1707 grams total) had the following composition:

| Component | Amount (g) | Wt % |
|---|---|---|
| LAROFLEX MP25 (polymer) | 13 | 0.76 |
| Copper pyrithione | 862 | 50 |
| Xylene solvent | 832 | 49 |

Evaluation of Copper Pyrithione Dispersion as an Inhalation Hazard

A copper pyrithione (CuPT) dispersion was made as described above with about 40% copper pyrithione and about 60% xylene. The copper pyrithione dispersion was evaluated in a test system designed to generate dust using cuprous oxide and talc as control materials, each of which is known to readily form dust with different densities and aerodynamic diameters. The testing procedures were as follows.

One pound of each material was weighed and added to an 8.5"×12"×2" open glass container. The glass containers with test materials were then set onto a shaker platform under a laboratory hood. Each test sample was monitored for dust using air-sampling trains consisting of a two-piece 37 mm binderless glass fiber filter cassette connected to a high volume air sampling pump operating at a calibrated flow rate of 1.0 liter of air per minute. These air-sampling trains were located at airborne capture points of 6 and 12 inches above the surface of each glass container.

Once the glass containers were secured, the shaker platforms were set to shake at 100 RPMs and the air-sampling trains were simultaneously turned on. Each test material remained on the shaker for 240 to 250 minutes. After 240 to 250 minutes, the shaker platform and air-sampling trains were turned off. The air-sampling trains were then post-calibrated and the air sampling filters were analyzed. Air samples taken from the copper pyrithione dispersion was analyzed for airborne copper pyrithione in the Analytical Department at Arch Chemicals, Inc. using an approved high pressure liquid chromatography (HPLC) method. Samples from the talc and cuprous oxide containers were submitted for analysis to CIGNA Environmental Health Laboratory, an AIHA accredited facility.

The above test procedures showed that the airborne particle density of the cuprous oxide control was 0.1 mg/m$^3$ at 6 inches from the surface of the material, and <0.042 mg/m$^3$ (limit of detection) at 12 inches from the surface of the material. Similarly, the airborne particle density of the talc control was 0.005 mg/m$^3$ at 6 inches from the surface of the material, and <0.004 mg/m$^3$ (limit of detection) at 12 inches from the surface of the material. In striking contrast, the airborne particle densities measured as a result of shaking the above copper pyrithione dispersion for 240 to 250 minutes at 100 RPM were <0.012 mg/m$^3$ (limit of detection) at both 6 and 12 inches. The results are summarized in the following Table:

| Material | Particle Density (6 inch) | Particle Density (12 inch) |
|---|---|---|
| Cuprous Oxide (Control) | 0.1 mg/m$^3$ | <0.042 mg/m$^3$ |
| Talc (Control) | 0.005 mg/m$^3$ | <0.004 mg/m$^3$ |
| Copper Pyrithione | <0.012 mg/m$^3$ | <0.012 mg/m$^3$ |

The results from the above comparison demonstrate that the copper pyrithione dispersion of the present invention has considerably less potential to generate significant airborne concentrations of copper pyrithione under normal conditions (e.g., shipping, handling, and the like). Under conditions that would normally generate dust of untreated copper pyrithione powder, the copper pyrithione that is a component of the composition of the present invention is not believed to pose an inhalation hazard under normal shipping and handling conditions.

While the invention has been described in combination with embodiments thereof, it is evident that many alternatives, modifications and variations will be apparent to those skilled in the art in light of the foregoing description. Accordingly, it is intended to embrace all such alternatives, modifications and variations as fall within the spirit and broad scope of the appended claims. All patent applications, patents, and other publications cited herein are incorporated by reference in their entireties.

What is claimed is:

1. A non-dusting copper pyrithione dispersion comprising: (a) from about 20% to about 99% by weight of solid copper pyrithione particles dispersed in (b) from about 0.05% to about 80% by weight of a liquid dispersant selected from the group consisting of water, organic solvents, and combinations thereof, said dispersion additionally comprising (c) from about 0.05% to about 30% by weight of a dust-inhibiting agent selected from the group consisting of surfactants, polymer resins, binders, and combinations thereof; wherein all weight percents are based upon the total weight of said composition, wherein said dust-inhibiting agent is present in the form of a polymer resin selected from the group consisting of acrylic resins, vinyl resins, alkyd resins, epoxy resins, polyurethane resins, natural resins, polyester resins, plastisols, and combinations thereof.

2. The non-dusting copper pyrithione dispersion of claim 1, wherein said polymer resin is a vinyl resin.

3. A non-dusting copper pyrithione dispersion comprising,:
    (a) from about 20% to about 99% by weight of solid copper pyrithione particles dispersed in (b) from about 0.05% to about 80% by weight of a liquid dispersant selected from the group consisting of water, organic solvents, and combinations thereof, said dispersion additionally comprising (c) from about 0.05% to about 30% by weight of a dust-inhibiting agent selected from the group consisting of surfactants, polymer resins, binders, and combinations thereof; wherein all weight percents are based upon the total weight of said composition; wherein said polymer resin is selected from the group consisting of acrylic resins, vinyl resins, alkyd resins, epoxy resins, polyurethane resins, natural resins, polyester resins, plastisols, and combinations thereof, and wherein said polymer resin comprises from about 0.2% to about 30% weight of said dispersion.

4. The dispersion of claim 3 wherein component (a) is present in the amount of from about 20% to about 70%.

5. A non-dusting copper pyrithione dispersion comprising: (a) from about 20% to about 99% by weight of solid copper pyrithione particles dispersed in (b) from about 0.05% to about 80% by weight of a liquid dispersant selected from the group consisting of water, organic solvents, and combinations thereof, said dispersion additionally comprising (c) from about 0.05% to about 30% by weight of a dust-inhibiting agent selected from the group consisting of surfactants, polymer resins, binders, and combinations thereof; wherein all weight percents are based upon the total weight of said composition; wherein said dust-inhibiting agent is present in the form of a binder selected from the group consisting of rosins, acrylates, xanthate or guar gums, polyvinyl alcohol, ethyl acetate, and combinations thereof.

6. A non-dusting copper pyrithione dispersion comprising: (a) from about 20% to about 99% by weight of solid copper pyrithione particles dispersed in (b) from about 0.05% to about 80% by weight of a liquid dispersant selected from the group consisting of water, organic solvents, and combinations thereof, said dispersion additionally comprising (c) from about 0.05% to about 30% by weight of a dust-inhibiting agent selected from the group consisting of surfactants, polymer resins, binders, and combinations thereof; wherein all weight percents are based upon the total weight of said composition; wherein said binder is selected from the group consisting of rosins, acrylates, xanthate or guar gums, polyvinyl alcohol, ethyl acetate, and combinations thereof and wherein said binder comprises from about 0.1% to about 20 wt %, based on the total weight of the dispersion.

7. The dispersion of claim 6 wherein component (a) is present in the amount of from about 20% to about 70%.

8. A non-dusting copper pyrithione dispersion comprising: (a) from about 20% to about 99% by weight of solid copper pyrithione particles dispersed in (b) from about 0.05% to about 80% by weight of liquid dispersant selected from the group consisting of water, organic solvents, and combinations thereof, said dispersion additionally comprising (c) from about 0.05% to about 30% by weight of a dust-inhibiting agent selected from the group consisting of surfactants, polymer resins, binders, and combinations thereof; wherein all weight percents are based upon the total weight of said composition; wherein said dispersant comprises water; and wherein said dispersion has a viscosity in the range of from about 1000 cps to about 7,500 cps at room temperature.

9. The dispersion of claim 8 wherein component (a) is present in the amount of from about 20% to about 70%.

10. A non-dusting copper pyrithione dispersion comprising: (a) from about 20% to about 99% by weight of solid copper pyrithione particles dispersed in (b) from about 0.05% to about 80% by weight of a liquid dispersant selected from the group consisting of water, organic solvents, and combinations thereof, said dispersion additionally comprising (c) from about 0.05% to about 30% by weight of a dust-inhibiting agent selected from the group consisting of surfactants, polymer resins, binders, and combinations thereof; wherein all weight percents are based upon the total weight of said composition; wherein said dispersant comprises a mixture of water and an organic dispersant; wherein said dispersion has a viscosity in the range of from about 5,000 cps to about 70,000 cps at room temperature.

11. The dispersion of claim 10 wherein component (a) is present in the amount of from about 20% to about 70%.

12. A non-dusting copper pyrithione dispersion comprising: (a) from about 20% to about 99% by weight of solid copper pyrithione particles dispersed in (b) from about 0.05% to about 80% by weight of a liquid dispersant selected from the group consisting of water, organic solvents, and combinations thereof, said dispersion additionally comprising (c) from about 0.05% to about 30% by weight of a dust-inhibiting agent selected from the group consisting of surfactants, polymer resins, binders, and combinations thereof; wherein all weight percents are based upon the total weight of said composition; wherein said dispersion is in the form of a paste.

13. The dispersion of claim 12 wherein component (a) is present in the amount of from about 20% to about 70%.

14. A non-dusting copper pyrithione dispersion, comprising an admixture of:

from about 20 to about 70 wt % of solid pyrithione particles;

from about 0.05 to about 30 wt % of a dust-inhibiting agent selected from the group consisting of surfactants, polymer resins, binders, and combinations thereof; and water as a dispersant;

wherein said dispersion has a viscosity in the range of from about 1000 cps to about 7,5000 cps at room temperature, wherein all weight percents are based on the total weight of said dispersion.

15. A non-dusting copper pyrithione dispersion, comprising an admixture of:

from about 20 to about 70 wt % of copper pyrithione;

from about 0.05 to about 30 wt % of a dust-inhibiting agent selected from the group consisting of surfactants, polymer resins, binders, and combinations thereof; and an organic dispersant selected from the group consisting of xylenes, alcohols, ethers, esters, and combinations thereof wherein said dispersion has a viscosity in the range of from about 5000 cps to about 70,000 cps at room temperature, wherein all weight percents are based on the total weight of said dispersion.

16. A dispersion of solid non-dusting copper pyrithione particles in a liquid dispersant, said copper pyrithione particles being coated with a coating compound selected from the group consisting of hydrocarbon resin monomer produced from co-polymerization of vinyltoluene and alpha-methylstyrene, rosins, polystyrene, cellulose, shellac, acrylic polymers, poly-D, L-lactic acid, poly-D, L-lactic-co-glycolic acid, zein, polymer esters of dicarboxylic acids, polyvinylacetate phthalate, polyvinyl alcohol, polyacrylic acid, ethyleneglycol, polyvinyl pyrrolidone, sodium lignosulfonate, chitosan, guar gums, polysaccharides, and combinations thereof, wherein greater than about 90% of said particles have sizes greater than 20 microns, and less than 10% of said particles have sizes less than or equal to 4 microns.

17. A method of making a non-dusting copper pyrithione dispersion, comprising the step of dispersing solid copper pyrithione particles in a liquid dispersant by combining (1) from about 20 to about 99 wt % of copper pyrithione;

(2) from about 0.05 to about 30 wt % of a dust-inhibiting agent selected from the group consisting of surfactants, polymer resins, binders, and combinations thereof; and (3) from about 0.05wt. % to about 80 wt % of a dispersant; to form said non-dusting copper pyrithione dispersion, wherein all weight percents are based on the total weight of said dispersion, wherein said dust-inhibiting agent is present as polymer resin selected from the group consisting of acrylic resins, vinyl resins, alkyd resins, epoxy resins, polyurethane resins, natural resins, polyester resins, plastisols, and combinations thereof.

18. A method of making a non-dusting copper pyrithione dispersion, comprising the step of dispersing solid copper pyrithione particles in a liquid dispersant by combining
   (1) from about 20 to about 99 wt % of copper pyrithione;
   (2) from about 0.05 to about 30 wt % of a dust-inhibiting agent selected from the group consisting of surfactants, polymer resins, binders, and combinations thereof; and
   (3) from about 0.05 wt. % to about 80 wt % of a dispersant; to form said non-dusting copper pyrithione dispersion, wherein all weight percents are based on the total weight of said dispersion;
   wherein said surfactant comprises from about 0.05 to about 10% by weight of said dispersion, wherein said surfactant comprises from about 0.5 to about 2% by weight of said dispersion, and wherein said polymer resin comprises from about 0.2% to about 30% by weight of said dispersion.

19. A method of making a non-dusting copper pyrithione dispersion, comprising the step of dispersing solid copper pyrithione particles in a liquid dispersant by combining
   (1) from about 20 to about 99 wt % of copper pyrithione;
   (2) from about 0.05 to about 30 wt % of a dust-inhibiting agent selected from the group consisting of surfactants, polymer resins, binders, and combinations thereof; and
   (3) from about 0.05 wt % to about 80 wt % of dispersant; to form said non-dusting copper pyrithione dispersion, wherein all weight percents are based on the total weight of said dispersion;
   wherein said binder is selected from the group consisting of rosins, acrylates, xanthate gums, and combinations thereof and wherein said binder comprises from about 0.1 to about 20 wt % to about 20 wt %, based on the total weight of the dispersion.

20. A method of making a non-dusting copper pyrithione dispersion, comprising the step of dispersing solid copper pyrithione particles in a liquid dispersant by combining
   (1) from about 20 to about 99 wt % of copper pyrithione;
   (2) from about 0.05 to about 30 wt % of a dust-inhibiting agent selected from the group consisting of surfactants, polymer resins, binders, and combinations thereof; and
   (3) from about 0.05 wt % to about 80 wt % of a dispersant; to form said non-dusting copper pyrithione dispersion, wherein all weight percents are based on the total weight of said dispersion;
   wherein said dispersant comprises water and wherein said dispersion has a viscosity in the range of from about 1000 cps to about 7,500 cps at room temperature.

21. A method of making a non-dusting copper pyrithione dispersion, comprising the step of dispersing solid copper pyrithione particles in a liquid dispersant by combining
   (1) from about 20 to about 99 wt % of copper pyrithione;
   (2) from about 0.05 to about 30 wt % of dust-inhibiting agent selected from the group consisting of surfactants, polymer resins, binders, and combinations thereof; and
   (3) from about 0.05 wt % to about 80 wt % of a dispersant; to form said non-dusting copper pyrithione dispersion, wherein all weight percents are based on the total weight of said dispersion,
   wherein said dispersant comprises one or more organic solvents, wherein said organic solvent is selected from the group consisting of xylenes, alcohols, ethers, esters, and combinations thereof and wherein said dispersion has a viscosity in the range of from about 5,000 cps to about 70,000 cps at room temperature.

22. A method of making a non-dusting copper pyrithione dispersion, comprising the step of dispersing solid copper pyrithione particles in a liquid dispersant by combining
   (1) from about 20 to about 99 wt % of copper pyrithione;
   (2) from about 0.05 to about 30 wt % of a dust-inhibiting agent selected from the group consisting of surfactants, polymer resins, binders, and combinations thereof; and
   (3) from about 0.05 wt. % to about 80 wt % of a dispersant; to form said non-dusting copper pyrithione dispersion, wherein all weight percents are based on the total weight of said dispersion and wherein said dispersion is in the form of a paste of said particles in said dispersant.

23. A method of making a non-dusting copper pyrithione dispersion, comprising the step of dispersing solid copper pyrithione particles in a liquid dispersant by combining
   (1) from about 20 to about 99 wt % of copper pyrithione;
   (2) from about 0.05 to about 30 wt % of a dust-inhibiting agent selected from the liquid dispersant by combining
   (1) from about 20 to about 99% of copper pyrithione;
   (2) from about 0.05 to about 30 wt % of dust-inhibiting agent selected from the group consisting of surfactants, polymer resins, binders, and combinations thereof; and
   (3) from about 0.05 wt. % to about 80 wt % of a dispersant; to form said non-dusting copper pyrithione dispersion wherein all weight percents are based on the total weight of said dispersion;
   further comprising the step of processing said dispersion into particles wherein at least about 90% have a particle size of less than 50 microns and further comprising the step of coating said particles with a coating compound selected from the group consisting of hydrocarbon resin monomer produced from co-polymerization of vinyl-toluene and alpha-methylstyrene, rosins, polystyrene, cellulose, shellac, acrylic polymers, poly-D, L-lactic acid, poly-D, L-latic-co-glycolic acid, zein, polymer esters of dicarboxylic acids, polyvinylacetate phthalate, polyvinyl alcohol, polyacrylic acid, ethylenenglycol, polyvinyl pyrrolidone, sodium lignosulfonate, chitosan, guar gums, polysaccharides, and combinations thereof.

* * * * *